(12) United States Patent
Virnig et al.

(10) Patent No.: US 6,231,784 B1
(45) Date of Patent: May 15, 2001

(54) WATER INSOLUBLE COMPOSITION OF AN ALDOXIME EXTRACTANT AND AN EQUILIBRIUM MODIFIER

(75) Inventors: Michael J. Virnig, Tucson, AZ (US); Phillip L. Mattison, North Wales, PA (US); Leroy O. Krbechek, Santa Rosa, CA (US); J. Murdoch Mackenzie, Gisborne (AU)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/063,235

(22) Filed: Apr. 20, 1998

Related U.S. Application Data

(63) Continuation-in-part of application No. 08/389,832, filed on Feb. 16, 1995, now abandoned.

(51) Int. Cl.$^7$ .................... C01B 31/00; C22B 15/00; C07C 275/00; C07C 261/00; C07C 271/00

(52) U.S. Cl. .................... 252/184; 423/24; 564/58; 564/215; 560/24; 560/157

(58) Field of Search .................... 423/24; 564/265, 564/58, 215; 252/184; 560/157, 24

(56) References Cited

U.S. PATENT DOCUMENTS

| | | | |
|---|---|---|---|
| 3,224,873 | 12/1965 | Swanson | 75/101 |
| 3,532,454 | 10/1970 | Fuhr et al. | |
| 3,627,813 | * 12/1971 | Abbate et al. | 560/24 |
| 3,887,679 | 6/1975 | Wigstol et al | 423/24 |
| 4,002,583 | 1/1977 | Taylor et al. | 106/285 |
| 4,142,952 | 3/1979 | Dalton | 204/106 |
| 4,173,616 | 11/1979 | Koenders et al. | 423/24 |
| 4,257,973 | 3/1981 | Mrowca | 260/413 |
| 4,433,151 | 2/1984 | Hiratani | 423/24 |
| 4,486,527 | 12/1984 | Kurisu et al. | 430/158 |
| 4,507,268 | * 3/1985 | Kordosky et al. | 423/24 |
| 4,978,788 | * 12/1990 | Dalton et al. | 423/24 |
| 5,024,821 | * 6/1991 | Greenshields et al. | 423/23 |
| 5,196,095 | 3/1993 | Sudderth et al. | 423/24 |
| 5,470,552 | 11/1995 | Kordosky et al. | 423/139 |
| 5,670,035 | * 9/1997 | Virnig et al. | 423/24 |

FOREIGN PATENT DOCUMENTS

| | | |
|---|---|---|
| 2 490 961 | 4/1982 | (FR) . |
| 2632658 | 12/1989 | (FR) . |
| 1 537 828 | 1/1979 | (GB) . |
| 2 183 078 | 5/1987 | (GB) . |
| 54-154719 | 12/1979 | (JP) . |
| 61-162597 | 7/1986 | (JP) . |
| WO92/08813 | 5/1992 | (WO) . |
| WO99/10546 | 3/1999 | (WO) . |

OTHER PUBLICATIONS

Organic Chemistry of Bivalent Sulfur, Reid, E.E., Chemical Pub. Co., Inc., vol. II, pp. 16–21, 24–29 (1960).
Organic Chemistry of Bivalent Sulfur, Reid, E.E., Chemical Pub. Inc., vol. III, pp. 11–14 (1960).
Chemical Abst. 67:74091, Van Veersen et al, 1997.
Chemical Abstract 116:148224, Pellmyr, et al, 1991.
Pellmyr, et al., "Cycad cone and angiosperm flora . . . ", Biochem, Systematics and Ecology, 19(8), 1991, pp. 623–627.
VanVeersen et al, "Zur Beziehungzwischen dem chemischem Aufbau . . . ", Kunstastoffe, 57(7), 1996. Jul., pp. 561–566.
Burkin, et al., "α–Substituted oxime Extractants–II . . . ", J. Ivory, Nacl. Chem, 1975, vol. 37, pp. 2187–2195.
Onaka, et al., "Reductive Coupling of S–(2–Pyridyl) Aliphatic . . . ", Chem. Lett., 1980, pp. 905–906.

* cited by examiner

*Primary Examiner*—Steven Bos
(74) *Attorney, Agent, or Firm*—John E. Drach; Patrick J. Span

(57) ABSTRACT

Alternative equilibrium modifiers for use with aldoxime extractants, such as hydroxyl aryl aldoxime extractants, employed in the process for extraction of metal values, particularly copper values, in the extraction from aqueous solutions, in which the extractant and modifiers are employed in an organic solvent phase, the solvent being a water insoluble, water immiscible hydrocarbon solvent, such as a kerosene.

30 Claims, 4 Drawing Sheets

WATER INSOLUBLE COMPOSITION OF AN ALDOXIME EXTRACTANT AND AN EQUILIBRIUM MODIFIER

CROSS-REFERENCE TO RELATED APPLICATIONS

This Application is a continuation-in-part application of U.S. application Ser. No. 08/389,832, filed Feb. 16, 1995, now abandoned, the disclosure of which is incorporated herein by reference the priority of which is claimed.

BACKGROUND OF THE INVENTION

1. Field of the Invention

This invention relates to the extraction of metal values from aqueous solutions and in particular to modifiers for aldoxime extractant employed for extraction of metals, particularly copper values.

2. Statement of Related Art

The present invention relates generally to solvent extraction processes for recovery of metal values from aqueous solutions and, more particularly, to formulative procedures for developing improved solvent extraction reagents and to the use of such reagents in recovery of, e.g., copper values.

The starting material for large scale solvent extraction processing of copper is an aqueous leach solution obtained from a body of ore which contains a mixture of metals in addition to copper. The leaching medium dissolves salts of copper and other metals as it trickles through the ore, to provide an aqueous solution of the mixture of metal values. The metal values are usually leached with sulfuric acid medium, providing an acidic aqueous solution, but can also be leached by ammonia to provide a basic aqueous solution.

The aqueous solution is mixed in tanks with an extraction reagent which is dissolved in an organic solvent, e.g., a kerosene. The reagent includes an extractant chemical which selectively forms metal-extractant complex with the copper ions in preference to ions of other metals. The step of forming the complex is called the extraction or loading stage of the solvent extraction process.

The outlet of the mixer continuously feeds to a large settling tank, where the organic solvent (organic phase), now containing the copper-extractant complex in solution, is separated from the depleted aqueous solution (aqueous phase). This part of the process is called phase separation. Usually, the process of extraction is repeated through two or more mixer/settler stages, in order to more completely extract the desired metal.

After extraction, the depleted aqueous feedstock (raffinate) is either discharged or recirculated to the ore body for further leaching. The loaded organic phase containing the dissolved copper-extractant complex is fed to another set of mixer tanks, where it is mixed with an aqueous strip solution of concentrated sulfuric acid. The highly acid strip solution breaks apart the copper-extractant complex and permits the purified and concentrated copper to pass to the strip aqueous phase. As in the extraction process described above, the mixture is fed to another settler tank for phase separation. This process of breaking the copper-extractant complex is called the stripping stage, and the stripping operation is repeated through two or more mixer-settler stages to more completely strip the copper from the organic phase.

From the stripping settler tank, the regenerated stripped organic phase is recycled to the extraction mixers to begin extraction again, and the strip aqueous phase is customarily fed to an electrowinning tank-house, where the copper metal values are deposited on plates by a process of electrodeposition. After electrowinning the copper values from the aqueous solution, the solution, known as spent electrolyte, is returned to the stripping mixers to begin stripping again.

Modifiers of extraction and stripping equilibria are frequently incorporated in those commercial reagent formulations which include the so-called "strong" extractants. Such extractants are capable of forming a very stable complex association with copper at quite low pH's and, consequently, require the use of very highly acidic aqueous stripping solutions in order to effect the breakdown of the copper-extractant complex. Where extreme acidity of stripping solutions generates problems in employing conventional electrodeposition processes, modifiers are incorporated to shift equilibria in a manner facilitating stripping at lower acidities and to enhance overall metal extraction efficiency. A wide variety of modifier chemicals has been proposed for use in formulation of solvent extraction reagents for copper. These have included: long chain ($C_6$ to $C_{20}$) aliphatic alcohols such as isodecanol, 2-ethylhexanol, and tridecanol; long chain alkyl phenols such as nonylphenol.

The use of kinetic additives and equilibrium modifiers has not been without drawbacks in the overall efficiency of solvent extraction processes in terms of the long range stability of reagents and the sensitivity of reagents to contaminants in aqueous feedstocks. Amines such as tertiary amines (Alamine® 336) are very strong modifiers of oximes but due to their tendency to transfer acid into the organic phase, amines also catalyze the hydrolysis of the oximes. However, by pairing a strongly acidic organic acid with the amine to form a salt, one can still achieve very strong modification of the oxime, while minimizing the rate of hydrolysis of the oxime. Also, as an example, while the minor proportion of kinetic additive present with the hydroxy aryl ketoxime extractant in the LIX®64N reagent formulation provides for kinetic enhancement in the use of the ketoxime, the additive is less stable toward hydrolytic degradation than the ketoxime. When used under operating conditions which are optimal for ketoxime extractant efficiency, the aliphatic α-hydroxy oxime thus tends to be depleted from continuous system more rapidly than the ketoxime. Similarly, hydroxy aryl aldoxime extractants are less stable in use than ketoximes and are rendered even more unstable by the presence of large quantities of nonylphenol. Alkyl phenol equilibrium modifiers, have also been noted to have severe deleterious effects on structural components of solvent extraction facilities, such as rubber linings, fittings, valves and the like.

In some cases, the combination of the modifier used in the extractant, with the contaminants present in the aqueous feedstock results in the generation of interfacial crud which must be continually removed from the solvent extraction circuit. In these cases, it is desirable to run with the minimum amount of modifier to achieve effective stripping and maximum net copper transfer, while at the same time, minimizing crud formation.

As is apparent from the foregoing, there exists a general need in the art for reagents for solvent extraction for the recovery of copper values which display efficient characteristics preferably with diminished quantities of additive or equilibrium modifiers. There is accordingly a need for modifiers which will provide increased net copper transfer by an extractant such as an aldoxime extractant.

U.S. Pat. No. 4,507,268 to Henkel Corporation describes extraction reagents formulated with various oxime extractants, including hydroxyaryl aldoxime extractants, which are employed in water immiscible organic solvents, such as kerosene, with certain equilibrium modifiers such as, phenols and alcohols (tridecanol, a commercially available branched chain alcohol) or tributyl phosphate. In defining the amount of modifier which would result in increased net copper transfer with the particular aldoxime employed, exemplified more particularly by 2-hydroxy-5-nonylbenzaldoxime, the patentee developed a "degree of modification" test. As employed there and herein, "degree of modification" designates the inverse ratio of (a) the stripped solvent copper level of an hydroxy aryl aldoxime extractant at equilibrium (expressed in terms of grams per liter of copper) extracted with an aqueous solution containing a fixed concentration of copper and sulfuric acid to (b) the stripped solvent copper level of the same extractant under the same conditions when a selected equilibrium modifier additive is present. Consistent with this definition, the presence of relatively small quantities of an equilibrium modifier will shift the extraction equilibrium slightly, resulting in minor diminution of aldoxime stripped solvent copper level at equilibrium, as will be reflected by a degree of modification value closely approaching 1.0, e.g., 0.99. Increased effective quantities of modifier under otherwise identical conditions will result in a more pronounced shift in extraction equilibrium and a more pronounced diminution of aldoxime stripped solvent copper level at equilibrium, as will be reflected by a degree of modification corresponding less than 1.0.

Expectedly the degree of modification resulting from a given molar ratio of equilibrium modifier to aldoxime in a reagent will vary depending on various factors, most significantly the chemical identity and nature of the equilibrium modifier, but also the conditions involved in determining the degree of modification of an aldoxime by a given equilibrium modifier. In U.S. Pat. No. 4,507,268 the following test conditions were to be adhered to for purposes of determining the degree of modification. The temperature at which the determination is made should be about 24° C. The molar concentration of aldoxime (or mixture of aldoximes) in the diluent should be about 0.184 as determined by copper loading and titration and an aldoxime stock of approximately 94 percent purity (with the remainder being substantially alkyl phenol starting material residue) should be employed. The diluent should be Escaid 100 or a mixture of aliphatic and aromatic hydrocarbons closely approximating the constitution of Escaid 100. An atomic absorption methodology should be employed for determining copper content. The composition of the strip solution should be 150 g/l sulfuric acid and 30 g/l $Cu^{+2}$.

U.S. Pat. No. 4,142,952 similarly employed a mixture of 5-nonylphenols as a modifier for oximes such as 5-nonyl or 5-heptyl salicylaldoxime.

More recently, U.S. Pat. No. 4,978,785 described the use of branched chain aliphatic or aromatic-aliphatic (or aliphatic) alcohols containing 14 to 30 carbon atoms or aliphatic or aromatic-aliphatic esters containing 10 to 30 carbon atoms wherein the ratio of the number of methyl carbon atoms to the number of non-methyl carbon atoms is higher than 1:5.

DESCRIPTION OF THE INVENTION

Figure 1:
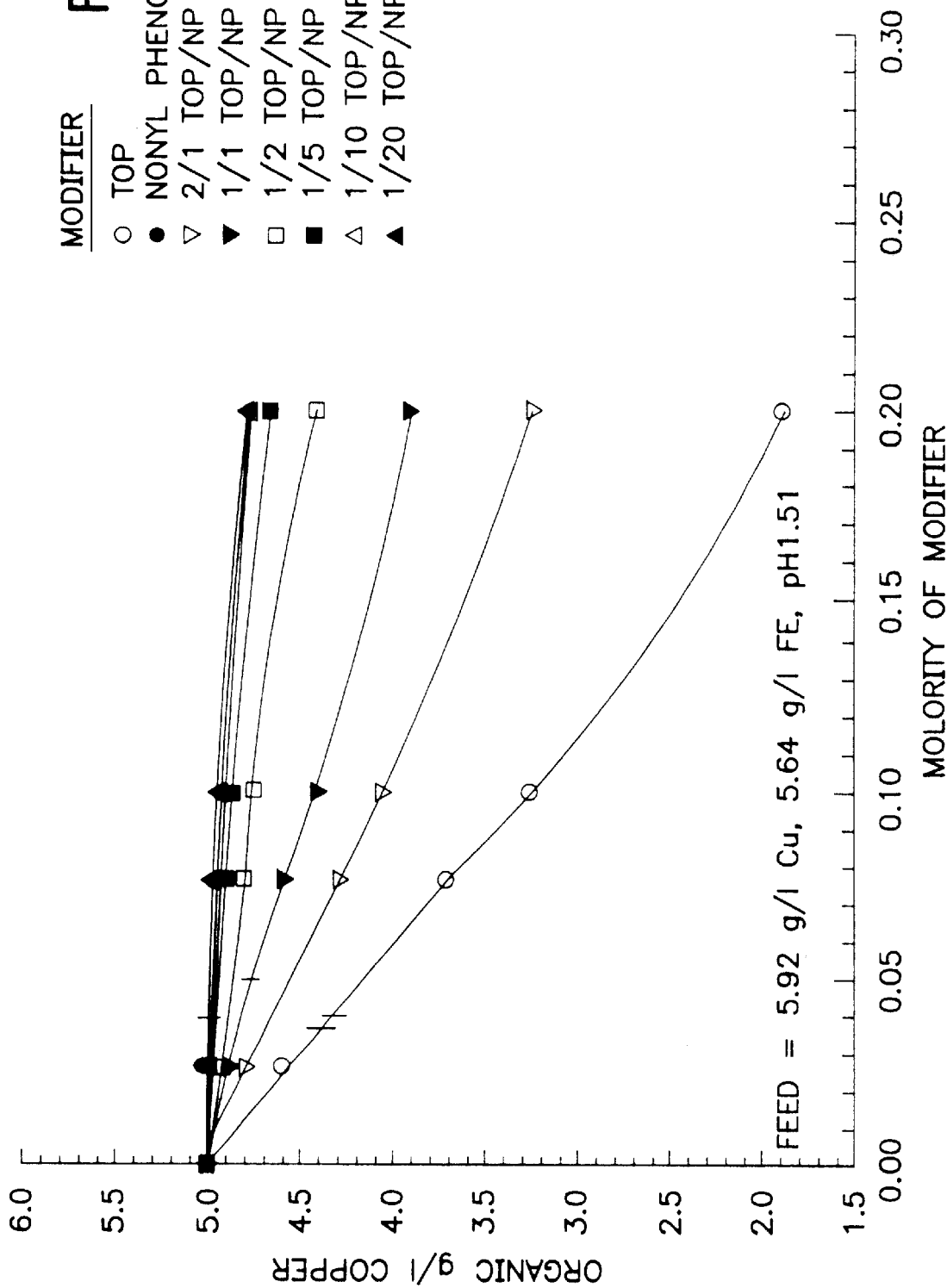
FIG. 1 is a graph representation of the modifier evaluation of extraction points of mixtures of nonylphenol (NP) and trioctylphosphate (TOP) with dodecyl salicylaldoxime extractant (DSAdO).

The present invention provides alternative equilibrium modifiers for use with aldoxime extractants such as the hydroxy aryl aldoxime extractants. Efficient copper recovery is achieved by reagents which comprise mixtures of hydroxy aryl aldoximes and the modifiers to be described hereafter in more detail.

Hydroxy aryl aldoxime extractants with which the modifiers of the present invention are particularly useful are those of the formula

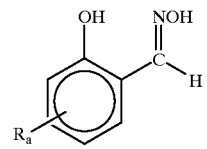

in which a has a value of 1, 2, 3 or 4, R is a saturated aliphatic group of about 1 to about 25 carbon atoms or an ethylenically unsaturated aliphatic group of 3 to about 25 carbon atoms, and the total number of carbon atoms in $R_a$ is from 3 to about 25. Preferred compounds are those wherein a is 1, and R is a straight or branched chain alkyl group having from about 7 to about 12 carbon atoms and wherein R is attached in a position para to the hydroxyl group. Among these, the more preferred are those wherein R is a mixture of isomers. Compounds which are especially useful include 2-hydroxy -5-heptylbenzaldoxime, 2-hydroxy -5-octyl benzaldoxime, 2-hydroxy -5-nonylbenzaldoxime and 2-hydroxy-5-dodecylbenzaldoxime.

In its broadest aspect, the present invention relates to reagent compositions, which are suitable for extracting copper from aqueous solutions containing copper values, i.e., copper salts, and to the process of extracting copper using such compositions. The extraction reagent compositions comprise a mixture of an hydroxy aryl aldoxime extractant and certain equilibrium modifiers in which the equilibrium modifier is present in an amount to provide a net copper transfer greater than that achieved by extraction with the aldoxime alone, without the presence of the modifier. If desirable to affect the kinetics, a kinetic additive may optionally also be included. Thus, in use the reagent composition may optionally contain a kinetic additive in an amount of 0 to about 20 mole percent based on the aldoxime content. Such kinetic additives are well known to those skilled in the oxime extraction art for extracting copper, such as those disclosed in U.S. Pat. No. 4,507,268 to Kordosky et al., including α-hydroxy oxime prepared according to Swanson, U.S. Pat. No. 3,224,873 or U.K. Patent 1,537,828 and α,β-dioximes according to Koenders et al., U.S. Pat. No. 4,173,616. A preferred α-hydroxy oxime kinetic additive is 5,8-diethyl-7-hydroxy dodecane-6-oxime and a preferred dioxime kinetic additive is a mixture of 1-(4'-alkylphenyl)-1,2-propanedione dioximes, according to Example 3 of U.S. Pat. No. 4,176,616.

As indicated in the Related Art section, in the past equilibrium modifiers for oxime copper extractant were the alkyl phenols in which the preferred alkyl group contained from about 7 to about 12 carbon atoms, long chain aliphatic alcohols containing from about 6 up to about 30 carbon atoms and organophosphorus compounds such as tributylphosphate (U.S. Pat. No. 4,507,268). U.S. Pat. No. 4,928,788 also describes as modifiers certain branched chain aliphatic or aromatic aliphatic alcohols containing 14 to about 30 carbon atoms and certain aliphatic or aromatic aliphatic esters containing from 10 to 30 carbon atoms, wherein the ratio of the number of methyl carbon atoms to the number of non-methyl carbon atoms is higher than 1:5.

The present invention accordingly provides alternative modifiers to those used in the past, which provide at least equivalent, and in many cases, improved results, in the net copper transfer, to those modifiers employed in the past. If desired, the present modifiers may optionally be employed in admixture with those used in the past to further modify the results.

As indicated, the modifiers of the present invention are employed in an amount to provide a net copper transfer greater than that achieved in the absence of the modifier. As in U.S. Pat. No. 4,507,268, the amount of modifier can be further defined by means of the degree of modification determined as described in that patent and as earlier noted in the Related Art section above. The useful and preferred range of degree of modification will vary dependent on the particular modifier compound and it is accordingly difficult to define a general range which will apply to all the individual modifiers, other than as the amount thereof being an amount effective to provide a net copper transfer greater than that achieved in the absence of the modifier. For example, in the case of the alkyl phenols, the most desirable, useful degree of modification range was from about 0.75 up to, but less than, about 1.0, preferably from about 0.90 and approaching, but not including 1.0, i.e., 0.99, whereas with modifiers other than the phenols, such as alcohols, like tridecanol, or alkylphosphates, such as tributylphosphate, the useful range of degree of modification may be from about 0.66 or even lower up to, but less than, 1.0.

The alternative modifiers of the present invention are a widely diverse group of compounds, including, but not limited to, certain simple carboxylic acid esters, oximes, nitriles, ketones, amides (carboxamides, sulfonamides or phosphoramides), carbamates, sulfoxides, ureas, and phosphine oxides, all of which are found to be efficient modifiers for aldoxime extractant reagents in the process of extracting copper values from aqueous solutions, particularly copper containing acid leach solutions.

The present invention accordingly has several aspects. Firstly, the invention is concerned with the reagent composition comprised of the water-insoluble aldoxime extractant formulated with at least one of the equilibrium modifiers noted earlier, optionally with a kinetic additive. Secondly, the reagents are formulated with organic solvent solution of water-insoluble, water immiscible aliphatic or aromatic solvents for use in a process for the recovery of a metal, preferably copper from aqueous solutions, typically acid solutions, which process comprises:

(1) contacting the metal-containing aqueous solution with an organic phase comprising the water immiscible solvent solution of the reagent composition to extract at least a portion of the metal values from the aqueous solution in to the organic phase;

(2) separating the resultant metal pregnant organic phase (O) from the resultant metal barren aqueous phase (A); and (3) recovering the metal value from the metal pregnant organic phase.

A wide variety of essentially water-immiscible liquid hydrocarbon solvents can be used in the copper recovery process of the present invention. These include aliphatic and aromatic hydrocarbons such as kerosene, benzene, toluene, xylene and the like. A choice of essentially water-immiscible liquid hydrocarbon solvents, or mixtures thereof for commercial operations will depend on a number of factors, including the plant design of the solvent extraction plant (mixer-settler units, Podbielnak™ extractors) and the like. The preferred solvents for use in the recovery process of the present invention, are the aliphatic and aromatic hydrocarbons having flash points of 130 degrees Fahrenheit and higher, and preferably at least 150°, and solubilities in water of less than 0.1% by weight. The solvents are essentially chemically inert. Representative commercial available solvents are Chevron™ ion exchange solvent (available from Standard Oil™ of California, having a flash point 195° F., Escaid™ 100 and 110 (available from Exxon-Europe having a flash point of 180° F.), Norpar™ 12 (available from Exxon-USA, flash point 160° F.), Conoco™-C1214 (available from Conoco, flash point 160° F.), Aromatic 150 (an aromatic kerosene available from Exxon-USA, flash point 150° F.), and the other various kerosene and petroleum fractions available from other oil companies.

In the process of the present invention, the organic solvent solutions will preferably contain from about 0.005 up to about 75% by weight of the aldoxime compounds, which typically will be employed at about 10–15%. Additionally, volume ratios of the organic:aqueous (O:A) phase will vary widely since the contacting of any quantity of the aldoxime organic solution with the copper containing aqueous leach solution will result in extraction of the copper values into the organic phase. For commercial practicality, however, the organic:aqueous phase ratios for extraction are preferably in the range of about 50:1 to 1:50.

After separation of the organic phase from the aqueous feed solution containing the copper, the copper is recovered from the organic phase by contacting the organic phase with an aqueous acid solution to strip the metal from the organic phase. Again, for commercial practicality, the organic:aqueous phase ratios are preferably in the range of about 50:1 to 1:50, after which the copper is recovered from the aqueous strip solution by conventional methods, typically electrowinning or precipitation.

The invention can be further illustrated by means of the following examples, in which all parts and percentages are by weight unless otherwise indicated. In the examples, the procedure for screening and evaluating the modifiers was as follows:

Degree of Modification

Definition:

The "degree of modification" is defined as the inverse ratio of (a) the stripped solvent copper concentration of an aldoxime extractant at equilibrium (g/l Cu) extracted from an aqueous solution containing 30 g/l Cu, 150 g/l $H_2SO_4$ to (b) the stripped solvent copper concentration of the same extractant under the same conditions when a selected equilibrium modifier is present.

Apparatus/Equipment

1. Analytical balance capable of weighing to ±0.1 mg.
2. Separatory funnels, 30 or 60 ml.
3. Volumetric flasks 21 & 100 ml.
4. Pipettes, 25 ml, 10 ml.
5. Filter paper Whatman 1PS phase separation paper
6. Atomic Absorption (AA) Spectrophotometer
7. pH meter Chemicals and Reagents
1. Copper sulfate pentahydrate, A.R.
2. Iron sulfate η-hydrate, A.R.
3. Sulfuric acid, A.R.
4. Escaid 100, Cork
5. (5-nonylsalicylaldoxime) approximately 94% pure

| Procedure: | | Details and Precautions: |
|---|---|---|
| A. Reagent Preparation | | |
| 1. Strip Solution | | |
| 30 g/l $Cu^{+3}$, 150 g/l $H_2SO_4$ | | |
| a) Weigh 117.85 gm of copper sulfate into a beaker and dissolve in 400 ml D.I. water and transfer to a 1 liter volumetric flask. | | |
| b) Add 150 gm conc. $H_2SO_4$ mix and cool to room-temperature. | | |
| c) Dilute to 1 liter with D.I. water. | | |
| d) Measure the copper as concentration by AA. Titrate with standardized NaOH solution for $H_2SO_4$ concentration | | Make adjustments necessary to bring the concentration of copper and $H_2SO_4$ to within ±0.5 gl of specified concentrations. |
| 2. Aldoxime Solution | | |
| 25 w/v % aldoxime in Escaid 100 | | |
| a) Weigh 265.96 gm of aldoxime into a beaker. dissolve in 400 ml Escaid 100 and transfer into a 1 liter volumetric flask. | | Wash the beaker with Escaid 100. |
| b) Dilute to 1 liter with Escaid 100 | | |
| 3. Modifier Solutions Preparation | | |
| Solutions are prepared at 0.00, 0.025, 0.100, 0.200 Molar modifier | | |
| a) Weigh the appropriate amount of modifier into a 100 ml volumetric flask. | | Weigh to ±0.001 gm of requested weight. Record the actual weight to 0.0001 gm. Recalculate the Molarity based on the actual weight to ±0.001 M. |
| b) Pipette 25 ml of 25 w/v % aldoxime into the volumetric flask. | | Allow the pipette to drain thoroughly. |
| c) Dilute to 100 ml with Escaid 100. | | Mix thoroughly. |
| 4. Feed Solution | | |
| 6 g/l Cu, 3 g/l Fe, pH 2.0 | | |
| a) Weigh 23.58 gm of $CuSO_4.5 H_2O$ and 14.25 gm of $Fe_2SO_4.nH_2O$ into a beaker and dissolve in 500 ml D.I. water. | | Mix on a magnetic stirrer until everything has dissolved. |
| b) Transfer to a 1 liter volumetric flask and dilute to 1 liter with D.I. water. | | Mix thoroughly. |
| c) Analyze by AA for copper and iron | | Adjust as required to correct copper and iron content content ±0.05 g/l. |
| d) Measure the pH. | | pH should be ±0.02 units of 2.00. Use conc. $H_2SO_4$ to adjust pH if necessary. Analyze and readjust . . . if needed. |
| B. Analysis | | |
| 1. Strip Point Determination | | |
| a) Pipette 10 ml of strip solution and 10 ml of modifier solution into a 30 or 60 ml separatory funnel. | | Can use a graduate instead of a pipette. |
| b) Shake for 3 minutes and let phases separate. | | |
| c) Drain aqueous phase and add 10 ml of fresh strip solution. | | |
| d) Repeat from b) above for a total of three contacts with fresh strip solution. | | |
| e) Filter the organic phase through 1PS paper. | | |
| f) Analyze the organic for copper concentration via AA. | | |
| 2. Max. Load | | |
| a) Pipette 10 ml of feed solution and 10 ml modifier solution into a 30 or 60 ml separatory funnel. | | |
| b) Shake for 3 minutes. | | |
| c) Drain the aqueous phase. | | |
| d) Add 10 ml fresh feed. | | |
| e) Repeat from b) above for a total of three contacts with fresh feed solution. | | |
| f) Filter the organic phase through 1PS paper. | | |
| g) Analyze the organic for copper and iron concentration via AA. | | |
| C. Reporting Results | | |
| 1. Calculate the degree of modification by dividing the strip point copper concentration by the strip point copper concentration of the Aldoxime alone. | | |
| 2. Plot the molarity of the modifier vs the strip point copper values. | | |
| 3. Plot the molarity of the modifier vs the max load points for copper and iron. | | |

EXAMPLE 1

1) The extraction isotherm point was determined by shaking 50 ml of fresh organic (0.188 M 5-nonylsalicylaldoxime and the indicated amount of modifier dissolved in Escaid 200, an aliphatic kerosene) with 50 ml of an aqueous feed solution containing 6 gpl of copper and 3 gpl of iron (III) as the sulfates with a pH of 1.9 for 30 minutes. The phases were separated, the organic was filtered, and then the copper content of the loaded organic phase was determined by atomic absorption spectroscopy.

2) The strip isotherm point was determined by shaking 25 ml of the loaded organic from point 1) above with 25 ml of a strip aqueous phase containing 30 gpl of copper and 170 gpl of sulfuric acid for 30 minutes. The phases were separated, the organic was filtered, and then the copper content of the stripped organic phase was determined by atomic absorption spectroscopy.

3) The net copper transfer is the difference between the extraction isotherm point and the strip isotherm point.

The net copper transfer effects of varying modifier and modifier concentration for a variety of modifiers can be seen from the following Table 1, in which nonylphenol, isotridecanol and tributylphosphate are included for comparison.

TABLE 1

Effects of varying Modifier and Modifier Concentration

| Modifier | Mole Ratio (Modifier/ Aldoxime) | Extract[1] [Cu] (gpl) | Strip[2] [Cu] (gpl) | Net[3] Cu Transfer (gpl) |
|---|---|---|---|---|
| None | — | 5.02 | 3.06 | 2.0 |
| Nonylphenol | 0.5 | 4.90 | 2.34 | 2.58 |
|  | 0.75 | 4.75 | 2.23 | 2.52 |
|  | 1.50 | 4.63 | 1.55 | 3.08 |
| Isotridecanol | 0.5 | 4.69 | 1.85 | 2.84 |
|  | 1.0 | 4.38 | 1.40 | 2.98 |
| Methyl | 0.25 | 4.81 | 2.56 | 2.25 |
| Iso-octanoate | 0.50 | 4.88 | 2.24 | 2.64 |
|  | 1.0 | 4.60 | 1.68 | 2.92 |
|  | 1.5 | 4.38 | 1.29 | 3.09 |
| Isodecyl Acetate | 0.25 | 4.90 | 2.59 | 2.31 |
|  | 0.50 | 4.67 | 2.30 | 2.37 |
|  | 1.00 | 4.34 | 1.59 | 2.75 |
|  | 1.50 | 4.30 | 1.11 | 3.19 |
| Dodecylaceto- | 0.25 | 4.72 | 2.60 | 2.12 |
| phenone Oxime | 0.50 | 4.72 | 2.48 | 2.26 |
| Oleonitrile | 0.25 | 4.78 | 2.22 | 2.56 |
|  | 0.60 | 4.45 | 1.59 | 2.86 |
|  | 0.75 | 4.14 | 1.61 | 2.83 |
|  | 1.00 | 4.12 | 0.92 | 3.20 |
| Isobutyl Heptyl | 0.25 | 4.81 | 2.73 | 2.08 |
| Ketone | 0.50 | 4.80 | 2.50 | 2.30 |
|  | 1.03 | 4.75 | 2.05 | 2.70 |
| N,N-Dimethyliso- | 0.25 | 4.28 | 1.73 | 2.56 |
| octanamide | 0.50 | 3.70 | 0.94 | 2.76 |
|  | 0.75 | 3.16 | 0.40 | 2.76 |
| N-tolyl Tridecyl- | 0.25 | 4.62 | 2.25 | 2.37 |
| carbamate | 0.60 | 4.28 | 1.55 | 2.73 |
|  | 0.75 | 4.01 | 1.20 | 2.81 |
| Di-2-ethylhexyl | 0.078 | 4.73 | 2.50 | 2.23 |
| Sulfoxide | 0.16 | 4.41 | 2.10 | 2.31 |
|  | 0.24 | 4.01 | 1.65 | 2.36 |
|  | 0.60 | 3.48 | 1.03 | 2.45 |
| Tributylphosphate | 0.125 | 4.50 | 2.37 | 2.12 |
| Decyltoluene- | 0.25 | 4.65 | 2.22 | 2.43 |
| sulfonamide | 0.60 | 4.60 | 1.85 | 2.75 |
|  | 1.0 | 4.15 | 1.25 | 2.90 |

Table 2, below, illustrates the net copper transfer as well as the degree of modification for a number of modifier additives.

TABLE 2

| Modifier Additive | Molarity | Strip Point | Net Transfer | Deg. of Mod. |
|---|---|---|---|---|
| None | 0.000 | 2.870 |  |  |
| Isobutyl iso- | 0.026 | 2.853 | 3.13 | 0.994 |
| octanoate | 0.100 | 2.350 | 3.59 | 0.819 |
|  | 0.200 | 1.868 | 3.98 | 0.651 |
| bis-2-Ethylhexyl | 0.025 | 2.231 | 3.61 | 0.777 |
| urea | 0.100 | 1.250 | 4.42 | 0.436 |
|  | 0.201 | 0.611 | 4.77 | 0.213 |
| N-propyl isotri- | 0.025 | 2.575 | 3.35 | 0.897 |
| decylcarbamate | 0.100 | 1.601 | 4.17 | 0.558 |
|  | 0.200 | 0.801 | 4.61 | 0.279 |
| N,N-bis-2-Ethyl- | 0.026 | 2.275 | 3.64 | 0.793 |
| hexylversatamide* | 0.104 | 0.863 | 4.74 | 0.301 |
|  | 0.208 | 0.223 | 4.81 | 0.078 |
| Isotridecanol | 0.024 | 2.602 | 3.34 | 0.907 |
|  | 0.125 | 1.683 | 4.05 | 0.586 |
|  | 0.250 | 1.027 | 4.68 | 0.358 |

*amide of Vesatic[n] acids - a mixture of highly branched, mainly tertiary monocarboxylic acids having an average of 10 carbon atoms, a boiling range of 140° C.–162° C. at 20 min, and a flash point of 120° C. (C.O.C.).

EXAMPLE 2

In substantially the same manner as Example 1, a number of modifier compounds were screened and evaluated for the effects of varying modifier concentrations which can be seen from Table 3 below. The modifier screening procedure in the interim was as follow:

Reagents

Strip solution: 30 g/l CU. 150 g/l $H_2SO_4$ in D.I. water.
Extraction solution: 6 g/l Cu, 6 g/l Fe, pH 1.50 in D.I water.

Procedure

Escaid 100 solutions of 0.176 molar DSAdO and modifier were prepared. The modifier levels tested were 0.025, 0.075, 0.10, and 0.20 molar. Each modifier solution and one additional solution containing only 0.176 molar DSAdO were tested as follows:

Strip Point 10 ml of the modifier solution was contacted three times for 3 minutes each with 10 ml of fresh strip solution. The resulting stripped organic was filtered through Whatman 1 PS paper and assayed for g/l Cu.

Extraction Point 5 ml of the above stripped organic was contacted one time for five minutes with 5 ml of extraction solution. The resulting loaded organic was filtered through 1 PS paper and assayed for g/l Cu.

Calculations

Degree of Modification—Divide g/l Cu in stripped organic by g/l Cu in unmodified stripped organic solution.

Net Transfer—Subtract g/l Cu in stripped organic from g/l Cu in loaded organic.

Most of the modifier compounds were available commercially; however, the carboxylic acid amides, carboxylic acid esters, the di-2-ethylhexyl sulfoxide, the alkyl carbonates, nonyl anisole, acetophenome oxime, oleo nitrile, benzyl-2-butoxy ethyl ether, benzyl 2-(2-butoxyethoxy) ethyl ether and the amine salts had to be prepared, though the amines and quarternary amines from which the salts were prepared were commercially available from Henkel Corporation. The preparation of these modifier compounds follow Table 3.

TABLE 3

Effects of Varying Modifier and Modifier Concentration

| Class | Modifier (Supplier) | Molar Ratio Modifier/ Aldoxime | Extract [Cu] (gpl) | Strip [Cu] (gpl) | Net Cu Transfer (gpl) |
|---|---|---|---|---|---|
|  | None |  | 5.12 | 2.87 | 2.25 |
| Alcohol | Isotridecanol | 0.142 | 4.98 | 2.53 | 2.45 |
|  |  | 0.426 | 4.63 | 1.88 | 2.75 |
|  |  | 0.568 | 4.51 | 1.65 | 2.86 |
|  | (Exxon) | 1.136 | 3.96 | 0.99 | 2.97 |
| Alcohol | Terpineol 101 | 0.142 | 4.96 | 2.46 | 2.50 |
|  |  | 0.426 | 4.68 | 1.94 | 2.74 |
|  |  | 0.568 | 4.53 | 1.73 | 2.80 |
|  | (Hercules) | 1.136 | 3.96 | 1.07 | 2.89 |
| Ester | 2,2,4-Trimethyl-1,3- | 0.142 | 4.96 | 2.38 | 2.58 |
|  | pentanediol | 0.426 | 4.70 | 1.90 | 2.80 |
|  | diisobutyrate | 0.568 | 4.56 | 1.70 | 2.86 |
|  |  | 1.136 | 4.11 | 1.09 | 3.02 |
|  | (Kodak) |  |  |  |  |
| Ester | Santicizer 97 | 0.142 | 4.98 | 2.36 | 2.62 |
|  | (Dialkyl adipate) | 0.426 | 4.63 | 1.82 | 2.81 |
|  |  | 0.568 | 4.52 | 1.60 | 2.92 |
|  | (Monsanto) | 1.136 | 4.07 | 1.00 | 3.07 |
| Ester | Dibutyl adipate | 0.142 | 4.85 | 2.30 | 2.55 |
|  |  | 0.426 | 4.61 | 1.78 | 2.83 |
|  |  | 0.568 | 4.50 | 1.58 | 2.92 |
|  | (Henkel KGaA) | 1.136 | 4.06 | 0.98 | 3.08 |
| Ester | Mixed adipates | 0.142 | 4.80 | 2.18 | 2.62 |
|  |  | 0.426 | 4.38 | 1.52 | 2.86 |
|  |  | 0.568 | 4.24 | 1.28 | 2.96 |
|  | (Dupont) | 1.136 | 3.46 | 0.69 | 2.77 |

TABLE 3-continued

Effects of Varying Modifier and Modifier Concentration

| Class | Modifier (Supplier) | Molar Ratio Modifier/ Aldoxime | Extract [Cu] (gpl) | Strip [Cu] (gpl) | Net Cu Transfer (gpl) |
|---|---|---|---|---|---|
| Ester | Diisobutyl adipate | 0.142 | 4.95 | 2.38 | 2.57 |
|  |  | 0.426 | 4.66 | 1.84 | 2.82 |
|  |  | 0.568 | 4.53 | 1.60 | 2.93 |
|  | (Dupont) | 1.136 | 4.04 | 1.00 | 3.04 |
| Ester | Isobutyl isooctanoate | 0.142 | 4.96 | 2.43 | 2.53 |
|  |  | 0.426 | 4.84 | 2.14 | 2.70 |
|  |  | 0.568 | 4.80 | 2.01 | 2.79 |
|  |  | 1.136 | 4.52 | 1.54 | 2.98 |
| Ester | 1,4-Butanediol dihexanoate | 0.142 | 4.93 | 2.28 | 2.65 |
|  |  | 0.426 | 4.62 | 1.76 | 2.86 |
|  |  | 0.568 | 4.50 | 1.55 | 2.95 |
|  |  | 1.136 | 4.08 | 0.96 | 3.12 |
| Ester | 1,6-Hexanediol dihexanoate | 0.142 | 4.92 | 2.27 | 2.65 |
|  |  | 0.426 | 4.60 | 1.71 | 2.89 |
|  |  | 0.568 | 4.47 | 1.50 | 2.97 |
|  |  | 1.136 | 3.96 | 0.87 | 3.09 |
| Ester | Methyl decanoate | 0.142 | 5.02 | 2.55 | 2.47 |
|  |  | 0.426 | 4.89 | 2.25 | 2.64 |
|  |  | 0.568 | 4.83 | 2.11 | 2.72 |
|  |  | 1.136 | 4.57 | 1.69 | 2.88 |
| Ester | 2-Pentyl octanoate | 0.142 | 4.97 | 2.49 | 2.48 |
|  |  | 0.426 | 4.83 | 2.17 | 2.66 |
|  |  | 0.568 | 4.75 | 2.02 | 2.73 |
|  |  | 1.136 | 4.55 | 1.66 | 2.89 |
| Ester | n-Hexyl hexanoate | 0.142 | 5.09 | 2.50 | 2.59 |
|  |  | 0.426 | 5.02 | 2.18 | 2.84 |
|  |  | 0.568 | 4.90 | 2.04 | 2.86 |
|  |  | 1.136 | 4.65 | 1.56 | 3.09 |
| Ester Ether | bis-2-Ethoxyethyl adipate | 0.142 | 4.78 | 2.07 | 2.71 |
|  |  | 0.426 | 4.20 | 1.28 | 2.92 |
|  |  | 0.568 | 4.00 | 1.02 | 2.98 |
|  |  | 1.136 | 2.81 | 0.48 | 2.33 |
| Ester Ether | EKTASOLVE DB Acetate | 0.142 | 4.87 | 2.31 | 2.56 |
|  |  | 0.426 | 4.51 | 1.65 | 2.86 |
|  |  | 0.568 | 4.36 | 1.37 | 2.99 |
|  | (Kodak) | 1.136 | 3.77 | 0.79 | 2.98 |
| Ester Ether | Benzoflex 9-88 Dipropylene glycol dibenzoate | 0.142 | 4.95 | 2.38 | 2.57 |
|  |  | 0.426 | 4.68 | 1.87 | 2.81 |
|  |  | 0.568 | 4.56 | 1.67 | 2.89 |
|  | (Velsicol) | 1.136 | 4.12 | 1.09 | 3.03 |
| Ester Ether | Benzoflex 400 Polypropylene glycol dibenzoate (x = 3) | 0.142 | 4.88 | 2.29 | 2.59 |
|  |  | 0.426 | 4.56 | 1.66 | 2.90 |
|  |  | 0.568 | 4.38 | 1.44 | 2.94 |
|  |  | 1.136 | 3.74 | 0.81 | 2.93 |
|  | (Velsicol) |  |  |  |  |
| Ester Ether | Benzoflex 284 Propylene glycol dibenzoate | 0.142 | 4.98 | 2.48 | 2.50 |
|  |  | 0.426 | 4.81 | 2.14 | 2.67 |
|  |  | 0.568 | 4.75 | 1.99 | 2.76 |
|  | (Velsicol) | 1.136 | 4.47 | 1.53 | 2.94 |
| Ester Ether | Benzoflex P-200 Polypropylene glycol dibenzoate (x = 4) | 0.142 | 4.53 | 1.99 | 2.54 |
|  |  | 0.426 | 3.58 | 1.14 | 2.44 |
|  |  | 0.568 | 2.82 | 0.81 | 2.01 |
|  |  | 1.136 | 1.52 | 0.33 | 1.19 |
|  | (Velsicol) |  |  |  |  |
| Ether | Diphenyl oxide | 0.25 | 4.80 | 2.93 | 1.87 |
|  | (Aldrich) | 0.50 | 4.93 | 2.87 | 2.06 |
| Ether | Nonyl anisole | 0.25 | 4.90 | 3.03 | 1.87 |
|  |  | 0.50 | 4.85 | 3.00 | 1.87 |
|  |  | 0.75 | 4.82 | 3.00 | 1.87 |
| Ether | Benzyl 2-(2-butoxyethoxy)ethyl ether | 0.142 | 4.84 | 2.23 | 2.61 |
|  |  | 0.426 | 4.42 | 1.54 | 2.88 |
|  |  | 0.568 | 4.18 | 1.24 | 2.94 |
|  |  | 1.136 | 3.51 | 0.63 | 2.88 |
| Ether | Benzyl 2-butoxyethyl ether | 0.142 | 4.87 | 2.37 | 2.50 |
|  |  | 0.426 | 4.64 | 1.90 | 2.74 |
|  |  | 0.568 | 4.55 | 1.76 | 2.79 |
|  |  | 1.136 | 4.17 | 1.20 | 2.97 |
| Carbonate | 2-Ethylhexyl carbonate | 0.142 | 4.81 | 2.27 | 2.54 |
|  |  | 0.426 | 4.71 | 2.07 | 2.64 |
|  |  | 0.568 | 4.68 | 1.96 | 2.72 |
|  |  | 1.136 | 4.50 | 1.63 | 2.87 |
| Carbonate | Isotridecyl carbonate | 0.142 | 4.85 | 2.28 | 2.57 |
|  |  | 0.426 | 4.67 | 2.03 | 2.64 |
|  |  | 0.568 | 4.70 | 1.94 | 2.77 |
|  |  | 1.136 | 4.45 | 1.58 | 2.86 |
| Carbonate | Lorol C8/C10 carbonate | 0.142 | 4.82 | 2.29 | 2.53 |
|  |  | 0.426 | 4.70 | 2.04 | 2.66 |
|  |  | 0.568 | 4.66 | 1.95 | 2.71 |
|  |  | 1.136 | 4.48 | 1.58 | 2.91 |
| Carbonate | Isobutyl carbonate | 0.142 | 5.06 | 2.58 | 2.48 |
|  |  | 0.426 | 4.94 | 2.32 | 2.62 |
|  |  | 0.568 | 4.88 | 2.20 | 2.68 |
|  |  | 1.136 | 4.67 | 1.78 | 2.89 |
| Ketone | Isobutyl heptyl ketone | 0.142 | 5.07 | 2.57 | 2.50 |
|  |  | 0.426 | 4.94 | 2.26 | 2.68 |
|  |  | 0.568 | 4.88 | 2.11 | 2.77 |
|  |  | 1.136 | 4.61 | 1.62 | 2.99 |
|  | (Kodak) |  |  |  |  |
| Ketone | Mixed higher ketones | 0.142 | 4.95 | 2.47 | 2.48 |
|  |  | 0.426 | 4.62 | 1.97 | 2.65 |
|  |  | 0.568 | 4.51 | 1.76 | 2.75 |
|  | (Union Carbide) | 1.136 | 3.93 | 1.13 | 2.80 |
| Ketone | Distilled mixed higher ketones | 0.142 | 4.98 | 2.48 | 2.50 |
|  |  | 0.426 | 4.80 | 2.16 | 2.64 |
|  |  | 0.568 | 4.79 | 2.05 | 2.74 |
|  | (Union Carbide) | 1.136 | 4.47 | 1.56 | 2.91 |
| Ketone | C11 ketone | 0.142 | 4.96 | 2.51 | 2.45 |
|  |  | 0.426 | 4.78 | 2.11 | 2.67 |
|  |  | 0.568 | 4.68 | 1.92 | 2.76 |
|  | (Kodak) | 1.136 | 4.29 | 1.39 | 2.90 |
| Ketone | 5,8-Diethyldodecane-6,7-dione | 0.142 | 5.14 | 2.70 | 2.44 |
|  |  | 0.426 | 5.10 | 2.52 | 2.58 |
|  |  | 0.568 | 5.04 | 2.36 | 2.68 |
|  |  | 1.136 | 4.94 | 2.19 | 2.75 |
| Nitrile | Undecyl cyanide | 0.142 | 5.00 | 2.55 | 2.45 |
|  |  | 0.426 | 4.81 | 2.28 | 2.53 |
|  |  | 0.568 | 4.80 | 2.15 | 2.65 |
|  | (Aldrich) | 1.136 | 4.17 | 1.72 | 2.45 |
| Nitrile | C21 Dinitrile | 0.142 | 4.96 | 2.37 | 2.59 |
|  |  | 0.426 | 4.69 | 1.86 | 2.83 |
|  |  | 0.568 | 4.62 | 1.68 | 2.94 |
|  |  | 1.136 | 4.17 | 1.09 | 3.08 |
| Nitrile | DN523 C36 Dinitrile | 0.142 | 4.98 | 2.42 | 2.56 |
|  |  | 0.426 | 4.74 | 1.87 | 2.87 |
|  |  | 0.568 | 4.62 | 1.67 | 2.95 |
|  | (Henkel Corp.) | 1.136 | 4.20 | 1.10 | 3.10 |
| Carbamate | N-Octyl isotridecyl-carbamate | 0.142 | 4.86 | 2.23 | 2.63 |
|  |  | 0.426 | 4.38 | 1.59 | 2.79 |
|  |  | 0.568 | 4.14 | 1.32 | 2.82 |
|  |  | 1.136 | 3.42 | 0.63 | 2.79 |
| Amide | N,N-bis-2-Ethylhexyl urea | 0.142 | 4.73 | 1.95 | 2.78 |
|  |  | 0.426 | 4.36 | 1.25 | 3.11 |
|  |  | 0.568 | 4.19 | 1.04 | 3.15 |
|  |  | 1.136 | 3.77 | 0.65 | 3.12 |
| Amide | N,N-bis-2-Ethylhexyl 2-ethylhexanamide | 0.136 |  | 2.44 |  |
|  |  | 0.543 |  | 1.18 |  |
|  |  | 1.087 |  | 0.32 |  |
| Amide | N-Hexyl 2-ethylhexanamide | 0.142 | 4.68 | 2.08 | 2.60 |
|  |  | 0.426 | 4.12 | 1.31 | 2.81 |
|  |  | 0.568 | 3.91 | 1.09 | 2.82 |
|  |  | 1.136 | 3.15 | 0.45 | 2.70 |
| Amide | N,N-Dibutyl 2-ethylhexanamide | 0.142 | 4.66 | 2.12 | 2.54 |
|  |  | 0.426 | 3.86 | 1.24 | 2.62 |
|  |  | 0.568 | 3.55 | 0.90 | 2.65 |
|  |  | 1.136 | 2.32 | 0.17 | 2.15 |
| Amide | N,N-Dibutyl benzamide | 0.142 | 4.89 | 2.24 | 2.65 |
|  |  | 0.426 | 4.14 | 1.31 | 2.83 |
|  |  | 0.568 | 3.80 | 0.94 | 2.86 |
|  |  | 1.136 | 2.76 | 0.22 | 2.54 |
| Amide | N,N-Dibutyl octanamide | 0.136 |  | 2.50 |  |
|  |  | 0.543 |  | 1.13 |  |
|  |  | 1.087 |  | 0.25 |  |

TABLE 3-continued

Effects of Varying Modifier and Modifier Concentration

| Class | Modifier (Supplier) | Molar Ratio Modifier/ Aldoxime | Extract [Cu] (gpl) | Strip [Cu] (gpl) | Net Cu Transfer (gpl) |
|---|---|---|---|---|---|
| Phosphate | Trioctylphosphate | 0.142 | 4.63 | 2.16 | 2.47 |
| | | 0.426 | 3.65 | 1.20 | 2.45 |
| | | 0.568 | 3.21 | 0.82 | 2.39 |
| | (ALFA Products) | 1.136 | 1.88 | 0.10 | 1.78 |
| Mixture | 1/2 molar ratio | 0.142 | 4.95 | 2.48 | 2.47 |
| | Trioctylphosphate/ | 0.426 | 4.76 | 2.12 | 2.64 |
| | Nonylphenol | 0.568 | 4.70 | 1.96 | 2.74 |
| | | 1.136 | 4.41 | 1.49 | 2.92 |
| Mixture | 1/1 molar ratio | 0.142 | 4.91 | 2.40 | 2.51 |
| | Trioctylphosphate/ | 0.426 | 4.61 | 1.90 | 2.71 |
| | Nonylphenol | 0.568 | 4.45 | 1.69 | 2.76 |
| | | 1.136 | 3.93 | 1.09 | 2.84 |
| Mixture | 2/1 molar ratio | 0.142 | 4.82 | 2.31 | 2.51 |
| | Trioctyl- | 0.426 | 4.32 | 1.67 | 2.65 |
| | phosphate/Nonyl- | 0.568 | 4.10 | 1.42 | 2.68 |
| | phenol | 1.136 | 3.21 | 0.65 | 2.56 |
| Mixture | 1/2 molar ratio | 0.142 | 4.77 | 2.27 | 2.50 |
| | Isotridecanol/ | 0.426 | 4.04 | 1.45 | 2.59 |
| | Trioctylphosphate | 0.568 | 3.70 | 1.12 | 2.58 |
| | | 1.136 | 2.58 | 0.32 | 2.26 |
| Mixture | 1/1 ratio | 0.142 | 4.84 | 2.31 | 2.53 |
| | Isotridecanol/ | 0.426 | 4.22 | 1.59 | 2.63 |
| | Trioctylphosphate | 0.568 | 3.92 | 1.29 | 2.63 |
| | | 1.136 | 2.97 | 0.49 | 2.48 |
| Mixture | 2/1 ratio | 0.142 | 4.93 | 2.36 | 2.57 |
| | Isotridecanol/ | 0.426 | 4.40 | 1.71 | 2.69 |
| | Trioctylphosphate | 0.568 | 4.16 | 1.45 | 2.71 |
| | | 1.136 | 3.40 | 0.71 | 2.69 |
| Mixture | 1/2 ratio Diisobutyl | 0.142 | 4.87 | 2.33 | 2.54 |
| | adipate/Isotri- | 0.426 | 4.63 | 1.83 | 2.80 |
| | decanol | 0.568 | 4.52 | 1.65 | 2.87 |
| | | 1.136 | 4.03 | 1.02 | 3.01 |
| Mixture | 1/1 ratio Diisobutyl | 0.142 | 4.89 | 2.29 | 2.60 |
| | adipate/Isotri- | 0.426 | 4.64 | 1.82 | 2.82 |
| | decanol | 0.568 | 4.51 | 1.61 | 2.90 |
| | | 1.136 | 4.02 | 1.00 | 3.02 |
| Mixture | 2/1 ratio Diisobutyl | 0.142 | 4.88 | 2.29 | 2.59 |
| | adipate/Isotri- | 0.426 | 4.64 | 1.80 | 2.84 |
| | decanol | 0.568 | 4.55 | 1.61 | 2.94 |
| | | 1.136 | 4.05 | 0.99 | 3.06 |
| Salt | 1/1 molar ratio | 0.142 | 4.37 | 1.93 | 2.44 |
| | Aliquat 336/ | 0.426 | 3.30 | 0.91 | 2.39 |
| | Dinonylnapthalene | 0.568 | 2.88 | 0.58 | 2.30 |
| | sulfonic acid | 1.136 | 1.71 | 0.08 | 1.63 |
| Salt | Alamine | 0.14 | 4.20 | 1.83 | 2.37 |
| | 308/Toluene- | 0.28 | 3.34 | 1.07 | 2.27 |
| | sulfonic acid | 0.42 | 2.69 | 0.59 | 2.10 |
| Salt | Alamine | 0.14 | 4.32 | 1.96 | 2.36 |
| | 336/Toluene- | 0.28 | 3.50 | 1.24 | 2.27 |
| | sulfonic acid | | | | |

The foregoing Tables and compounds exemplified therein, evaluated as modifiers with (5-nonyl salicylaldoxime) as the extractant in kerosene solution (Escaid 100) for the extraction of copper from aqueous acid solutions containing copper, clearly illustrate a large number of compounds which may be employed as modifiers for an aldoxime extractant.

As can be seen therefrom, a number of compounds provide for net copper transfer at least equivalent to those employed in the past, such as nonylphenol, tridecanol and tributyl phosphate, while others provide for a significant increase in the net copper transfer. It can be seen that in the absence of any modifier, with a degree of modification of 1.0, a net copper transfer of 2.0 g/l results. The nonylphenol and tridecanol employed in the past, which are included in the Tables for comparison resulted in an increase in the net copper transfer up to about 3 g/l copper, employing the modifier in amounts of about 0.5 to about 1.5 moles of modifier per mole of aldoxime. The tributylphosphate, however, showed only a small increase in the net copper transfer. In contrast, many of the compounds of the present invention showed net copper transfer increases to above 3.0, and even exceeding 4.0 g/l at molarities varying from about 0.02 to about 0.25 with degrees of modification from about 0.2 up to about 0.95. In general, the mole ratio of modifier/ aldoxime will typically vary from about 0.2 to about 1.5, preferably from about 0.5 to about 1.2. The degree of modification will vary dependent on the particular modifier and aldoxime employed as the extractant. Typically however, the degree of modification as defined herein will vary between about 0.25 and approach 1.0, i.e., up to about 0.99, and preferably within the range of about 0.3 to about 0.9.

From Table 3 in particular, it can be seen that suitable modifiers fall within a variety of diverse classes of compounds, such as, alcohols and esters, polyethers, ester-ethers, oximes, ketones, nitriles, carbonates carbamates, amides, and salts of certain amine (trialkyl amines) and quaternary ammonium compounds, which modifier compounds contain aliphatic, aromatic or araliphatic groups having from about 4 to about 36 carbon atoms, the total number of carbon atoms in the compounds being sufficient to render the compounds water insoluble and soluble in the water insoluble and water immiscible hydrocarbon solvents employed for use with the water insoluble aldoxime. Excluded from the scope of the present invention are alcohol and ester classes of modifier compounds such as tridecanol other than (a) alkanols containing up to 20 carbon atoms, and those (b) long chain branched alcohols and esters having up to 30 carbon atoms with a ratio of methyl groups to non-methyl groups above 1:5. It should be understood however, that the modifier compounds of the present invention may, if desired, be employed admixed with the modifiers employed in the past, such as phenols, tridecanol and other fatty alcohols and tributylphosphate, the highly branched alcohols or esters having a ratio of methyl to non-methyl groups above 1:5.

For the purposes of the present invention, also excluded from the ether class is nonyl anisole. While, based on the other ethers exemplified, nonyl anisole might be expected to be useful as a modifier, as can be seen from Table 3 in particular, nonyl anisole appears to have an adverse effect on net copper transfer, showing a net copper transfer of only 1.87 g/l at mole ratios of modifier to aldoxime from 0.25 to 0.75, thus being substantially ineffective in view of the fact that the absence of any modifier resulted in a net copper transfer of 2.0 g/l. This does serve to illustrate however the unpredictability from one compound to another as to its utility as a modifier for aldoxime extractants in the process of recovery of copper from aqueous solutions containing copper, particularly aqueous acid solutions.

As indicated earlier, many of the compounds evaluated herein are commercially available and suppliers of many of the compounds have been noted. Where the compounds were not commercially available, it was necessary to prepare the compounds in the various classes as described in the following examples 3 through 16.

EXAMPLE 3

Preparation of Carboxylic Acid Amides

The carboxylic acid amides were synthesized by a typical Schotten-Baumann type procedure. The desired starting amine (0.8 mole) and triethylamine (0.8 moles) were placed in a one liter round bottom flask fitted with a mechanical stirrer, addition funnel, and thermometer. The mixture was stirred and the corresponding carboxylic acid chloride (0.6 moles) added over a period of 30 minutes. Toluene was added as needed to keep the reaction mixture stirrable. The temperature was allowed to rise to 85° C. After addition was complete, the reaction mixture was allowed to stir for an additional 1–2 hours. The mixture was then cooled, washed three times with equal volumes of 5% by weight aqueous sodium bicarbonate solution and then three times with equal volumes of water. The product was then distilled under vacuum. The heartcut was identified by IR and NMR spectroscopy.

EXAMPLE 4

Preparation of Carboxylic Acid Esters

The carboxylic acid esters were prepared by a strong acid catalyzed condensation of the carboxylic acid with the alcohol. The carboxylic acid (0.7 moles), alcohol (0.85 moles), p-toluenesulfonic acid (0.5 g) and toluene (25 ml) were placed in a 500 ml round bottom flask fitted with a stirrer and a Dean Stark trap for water removal. The reaction mixture was heated to reflux and then held at reflux until the theoretical amount of water had been collected. The reaction mixture was then cooled, washed twice with 5% by aqueous sodium carbonate and twice with water. The crude product was then fractionally distilled under vacuum. The heartcut was collected and its identity confirmed by IR and NMR spectroscopy.

EXAMPLE 5

Di-2-Ethylhexyl Sulfoxide

The starting sulfide was prepared by the reaction of 2-ethylhexyl chloride with sodium sulfide (See Reid, "Organic Chemistry of Bivalent Sulfur", Vol. 2, pp 16–21, 24–29, and Vol 3, pp 11–14 (1960)). The di-2-ethylhexylsulfide (0.775 moles) and acetone (1500 ml) were then placed in a magnetically stirred flask and 30% hydrogen peroxide added over a period of 10 minutes. The reaction mixture was allowed to stir at room temperature for 48 hours. A 10% by weight aqueous solution of sodium bisulfite (350 ml) was then added to the flask along with 350 ml of water. The resultant mixture was extracted with ether. The ether extract was washed with water, then saturated sodium chloride solution, dried and evaporated to a clear oil. IR analysis established that oxidation was not complete and the entire procedure was repeated. The final product was judged to be of high quality based on IR analysis.

EXAMPLE 6

Preparation of Alkyl Carbonates

The alkyl carbonates were prepared by transesterification of dimethyl carbonate with a higher molecular weight alcohol. A mixture of the alcohol (4.1 moles), dimethyl carbonate (2.0 moles) and potassium carbonate (0.84 g) was heated to reflux and the methanol was slowly distilled away. The excess alcohol and unreacted dimethyl carbonate were then removed under vacuum and the product distilled under vacuum. The product was identified by IR and NMR spectroscopy.

EXAMPLE 7

Preparation of Salts

The amines, Alamine® 308 (trioctyl amine) or 336 (trialkyl amine having $C_8$, $C_{10}$ groups) available from Henkel Corp., were dissolved in kerosene and an equimolar amount of p-toluenesulfonic acid, available from Aldrich, was then added. The salt settled out as a thick oil which was then used to make up the test solutions. The salt of Aliquats® 336 (methylquat of Alamine® 336), available from Henkel Corp, with dinonylnapthalenesulfonic acid, available from Pfaltz and Bauer, was prepared by mixing equivalent amounts of the Aliquat 336 with the acid in kerosene and washing with dilute sodium bicarbonate solution.

EXAMPLE 8

Nonyl Anisole

Nonyl anisole was prepared from nonylphenol, available from Jefferson Chemicals, and methyl iodide under typical Williamson ether synthesis conditions. Nonylphenol (1.0 mole), methyl iodide (1.2 moles), potassium carbonate (1.25 moles) and acetone were placed in a round bottom flask and heated to reflux. After refluxing overnight, the reaction mixture was poured into water and extracted with ether. The ether extract was washed with saturated sodium chloride solution, dried and evaporated to an oil which was then purified by vacuum distillation. The product was analyzed as nonyl anisole by IR and NMR spectroscopy.

EXAMPLE 9

Dodecylacetophenone Oxime

Dodecylacetophenone oxime was prepared as described in European patent Application 557274.

EXAMPLE 10

Preparation of C21 Dinitrile

A mixture of 500 g of C21 diacid from Westvaco, 3.0 g of zinc oxide and 3 g of water was charged to a 1.5 liter reactor and heated to 150° C. Anhydrous ammonia was sparged through the hot mixture. The temperature was raised to 295–300° C. with continuous sparging with ammonia. The reaction mixture was kept at these conditions for a total of 9 hours during which time about 125 ml of aqueous and organic components were collected in a Dean Stark trap. An additional 5.0 g of zinc oxide was added and the mixture distilled. Fraction I, BP 150–195° C. @ 0.6–0.95 mm, weighed 78 g. Fraction II, BP 195–215° C. @ 0.65 mm, weighed 177 g. Both fractions were considered by GC/IR to be a mixture of isomeric nitriles which were free of carboxylic acids.

EXAMPLE 11

Oleonitrile

Oleonitrile was prepared from oleic acid in same fashion as was the C-21 dinitrile above.

EXAMPLE 12

Preparation of Benzyl 2-Butoxyethyl Ether

A mixture of 8.1 g of 60% sodium hydride (0.2 moles) in mineral oil, 20 ml of toluene and 100 ml of tetrahydrofuran was prepared. To this 23.6 g of 2-butoxyethanol (0.2 moles) was added over a 5 minute period of time. The resultant mixture was heated at reflux temperature for one hour after which 25.2 g of benzylchloride (0.2 moles) was added. The reaction mixture was heated at reflux temperature for an additional hour. Any unreacted sodium hydride was destroyed by the addition of 10 ml of methanol. The cooled reaction mixture was diluted with hexane and washed with water. The aqueous phase was back washed with hexane which was combined with the first hexane extract and stripped of volatiles at reduced pressure to leave 44 g of product which contained about 80% benzyl-2-butoxyethyl ether, 6% 2-butoxyethanol, 7% benzylchloride and 3% methyl benzyl ether. This was distilled to yield 1.4 g of forecut, BP to 80° C. @ 0.6 mm which was discarded and 34 g of heart cut, BP 80° C. @ 0.6 mm. The heart cut was judged to contain about 91% desired product.

EXAMPLE 13

Preparation of Benzyl 2-(2-Butoxyethoxy) Ethyl Ether

A mixture of 8.25 g of 60% sodium hydride (0.205 moles) in mineral oil, 20 ml of toluene and 100 ml of tetrahydrofuran was prepared. To this 32.4 g of 2-(2-butoxyethoxy) ethanol was added over a 5 minute period of time. The resultant mixture was heated at reflux temperature for 3.5 hours before all the sodium hydride had reacted, after which 25.2 g of benzylchloride (0.2 moles) was added. This mixture was heated at reflux temperature for an additional hour. Any unreacted sodium hydride was destroyed by the addition of 10 ml of methanol. The cooled reaction mixture was extracted with water and the volatiles removed from the organic phase at reduced pressure to leave 53 g of product which was judged to contain about 84% benzyl-2-(2-butoxyethoxy) ethyl ether, 3% toluene, 2% methyl benzyl ether and 3% benzylchloride. This was distilled to yield 4.9 g of forecut, BP to 90° C. @ 0.5 mm which was discarded and 43.5 g of heart cut, BP 90–98° C. @ 0.3 mm. The heart cut was judged to be about 97% pure.

EXAMPLE 14

Preparation of Bis-2-Ethylhexylurea

A mixture of 1,592 g (12.3 moles) of 2-ethylhexylamine and 261 g (4.35 moles) of urea was heated at reflux temperature for 24 hr. The mixture was cooled and about 420 g of 2-ethylhexyl amine was removed by distillation at pot temperatures of 115–200° C./1 mm pressure. The residue was subject to a two pass distillation on a wiped film evaporator. The first pass produced 112 g of distillate at 200° C./0.3 mbar pressure which was discarded. The residue was distilled at 230° C. /0.25 mbar to produce 1,035 g of product.

EXAMPLE 15

Preparation of 5,8-Diethyldodecane-6,7-Dione

A mixture of 67 g of 5,8-diethyl-7-hydroxy-6-dodecanone (acyloin) and 0.5 g of 86% potassium hydroxide pellets was heated to 185–190° C. for 7 hours while air was bubbled through the system. Analysis by infrared showed the residue to be about 11% acyloin and 79% 5,8-diethyldodecane-6,7-dione (diketone).

A mixture of 114 g of acyloin and 2.0 g of 86% potassium hydroxide pellets was heated to 195–200° C. Air was bubbled through for 6 hours at that temperature in the presence of stainless steel screen. Analysis by GC/IR showed the material to be about 89% diketone and 4% acyloin.

Two such preparations were combined, diluted with hexane, washed with alkali then water and stripped of volatiles at reduced pressure to leave 96 g. This was distilled through a column packed with rashig rings at 2–5 MM pressure.

Cut I, BP to 135° C., 3.7 G discarded.

Cut II, BP 135–145° C., 60 G; GC/IR showed 1% acyloin and 92% diketone.

Cut III 145° C./1 mm pressure, 16 g; GC/IR found 10% acyloin and 78% diketone.

EXAMPLE 16

Preparation of N-n-Octyl Isotridecylcarbamate

A mixture of 50 g (0.32 mole) of octyl isocyanate, 75 g (0.38 moles) of isotridecyl alcohol, 1.0 ml of pyridine and 60 ml of toluene was heated at reflux temperature for 20 hours. The volatiles were removed at reduced pressure to leave 124 g. The residue was distilled at about 1 mm pressure to produce 16.4 g of forecut BP to 165° C. which was discarded. The heart cut, at 165° C., produced 106.7 g of product which was considered to be of very high purity by IR and NMR analyses.

N-tolyl isotridecylcarbamate can be produced in a similar manner from p-tolyl isocyanate and isotridecyl alcohol.

EXAMPLE 17

Figure 2:
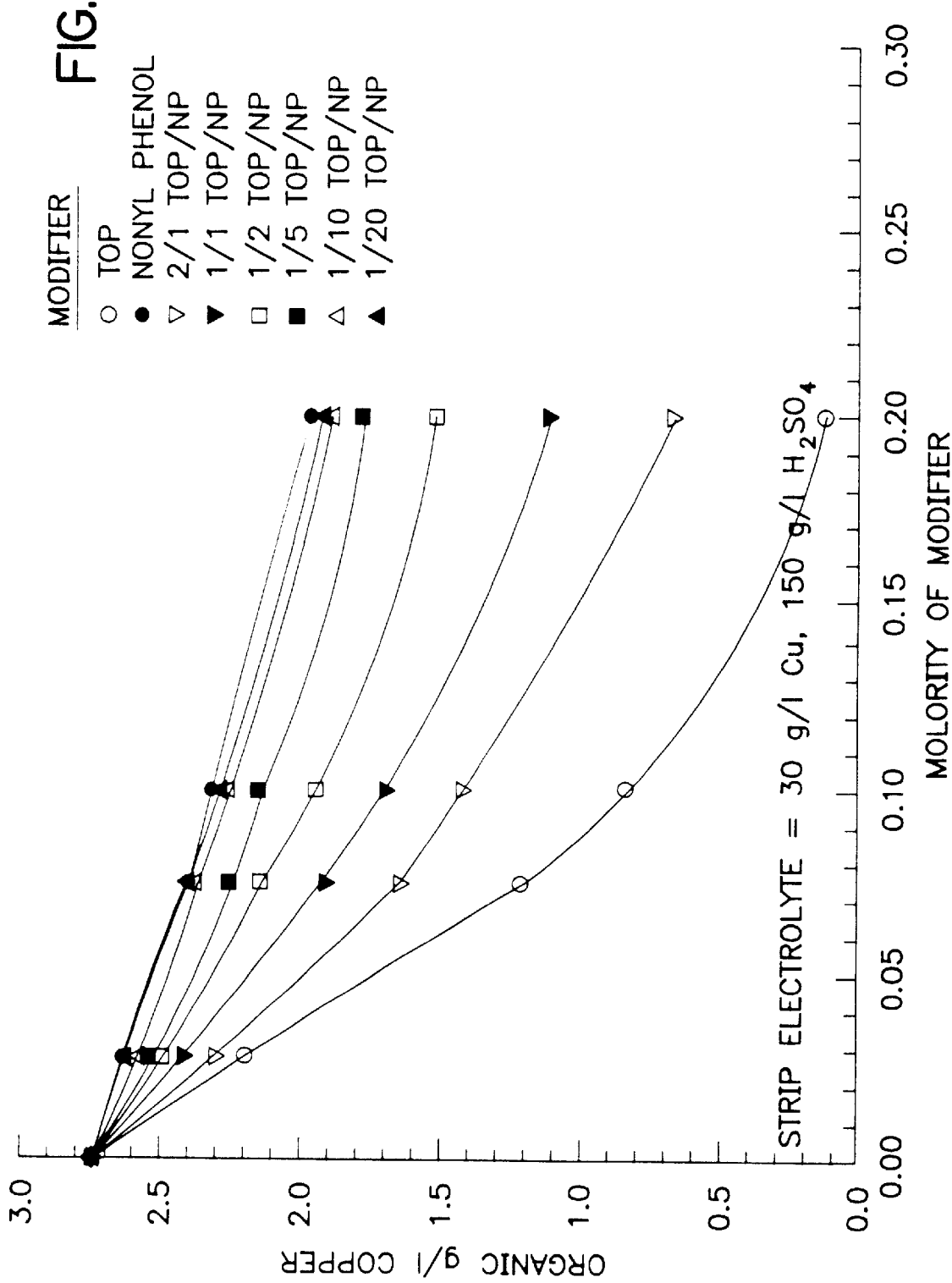
FIG. 2 is a similar graph representation of the strip point of the mixture of NP and TOP.
Figure 3:
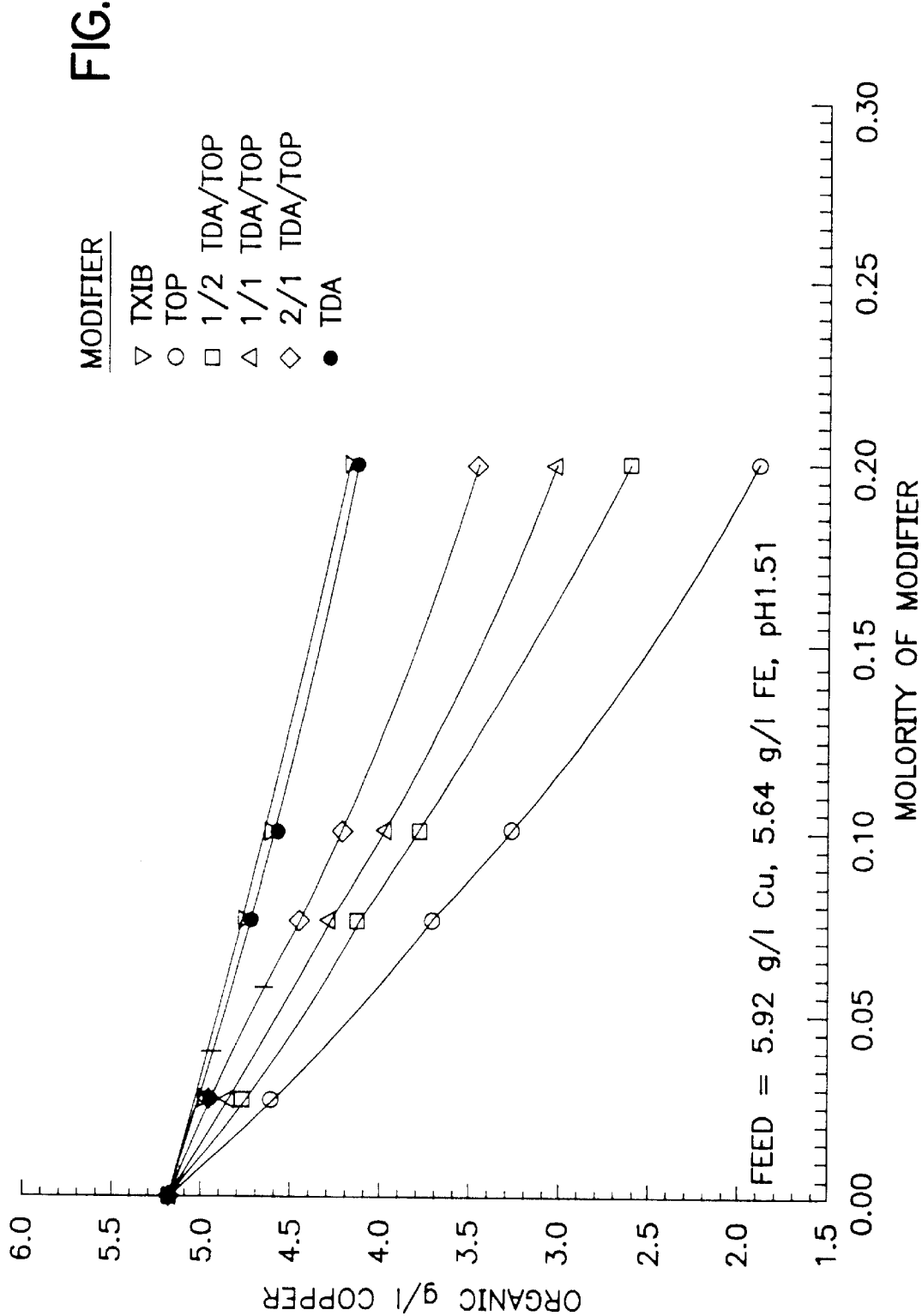
FIG. 3 is another graph representation of the modifier evaluation extraction points of mixtures of isotridecanol (TDA) and trioctylphosphate (TOP) with dodecylsalicylaldoxime extractant (DSAdO).
Figure 4:
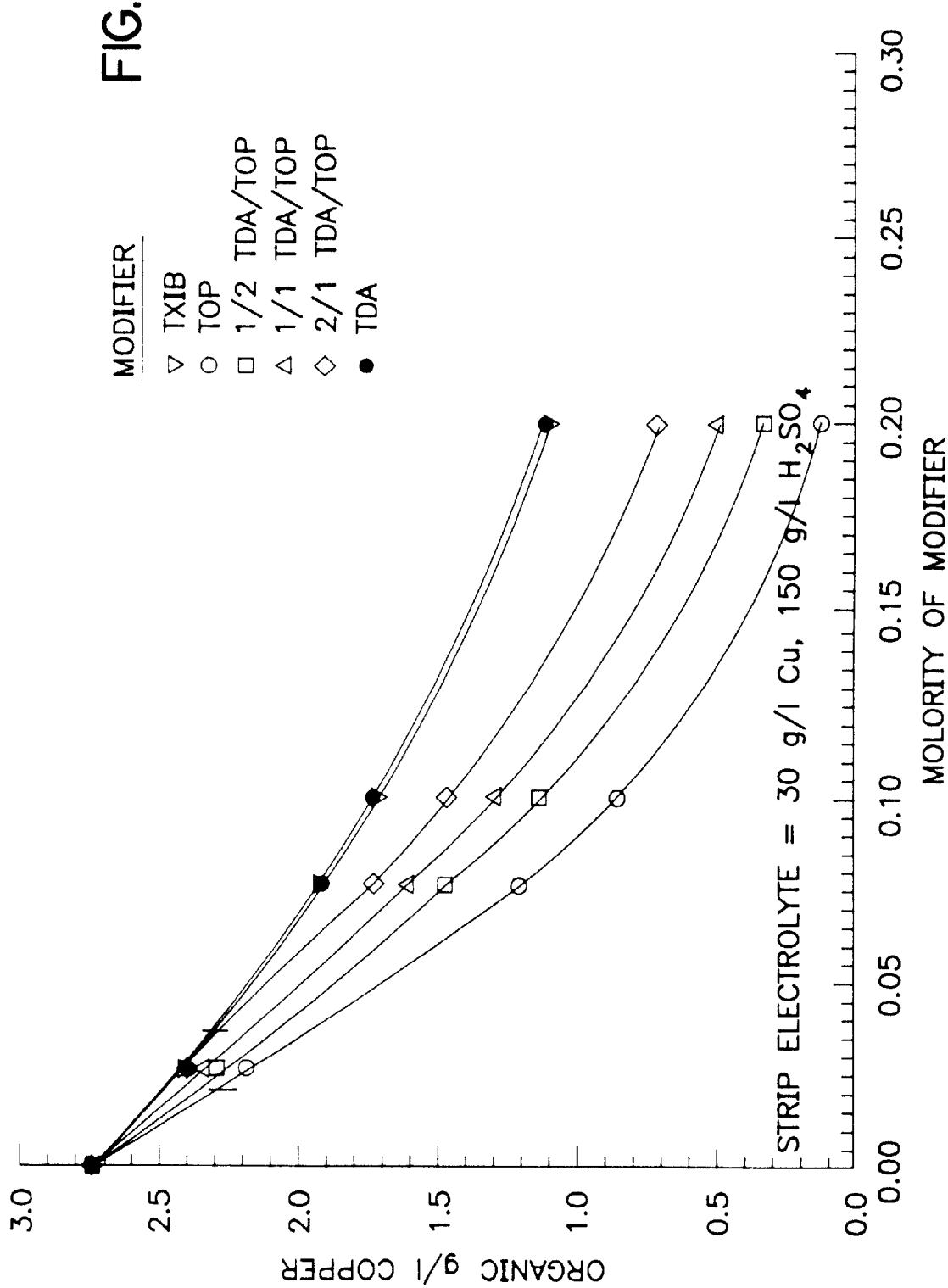
FIG. 4 is a similar graph representation of the modifier strip point of the mixtures of TDA, and TOP with DSAdO.

Earlier in this application, reference was made to the problem of crud formation in that it is desirable to run with the minimum amount of modifier necessary to achieve effective stripping and maximum net copper transfer while at the same time minimizing crud formation. One potential way of achieving the foregoing is to use mixtures of modifiers. Accordingly, mixtures of trioctylphosphate with either nonylphenol or isotridecanol were evaluated, following the procedure employed in Example 2. The results can be seen in Table 4 below and in FIGS. 1 through 4.

TABLE 4

Mixtures of strong Hydrogen Bond Acceptors with Hydrogen Bond Donors as Modifiers

| Modifier | Molar Ratio Modifier/ Aldoxime | Extract [Cu] (gpl) | Strip [Cu] (gpl) | Net Cu Transfer (gpl) |
|---|---|---|---|---|
| Nonylphenol | 0.213 | 5.0 | 2.55 | 2.45 |
|  | 0.426 | 4.95 | 2.40 | 2.55 |
| Trioctylphosphate | 0.11 | 4.75 | 2.27 | 2.48 |
|  | 0.213 | 4.37 | 1.90 | 2.47 |
|  | 0.426 | 3.65 | 1.20 | 2.45 |
| Isotridecanol | 0.213 | 4.87 | 2.3 | 2.57 |
|  | 0.426 | 4.63 | 1.88 | 2.75 |
| 1/1 Nonylphenol/ Trioctylphosphate | 0.426 | 4.60 | 1.90 | 2.70 |
| 1/1 Isotridecanol/ Trioctylphosphate | 0.426 | 4.22 | 1.59 | 2.63 |
| 2/1 Isotridecanol/ Trioctylphosphate | 0.340 | 4.60 | 1.90 | 2.70 |

The data for points at molar ratios of 0.11, 0.213 and 0.34 were derived by graphical interpolation of the data in the graphs in FIGS. 1 through 4, summarizing the results for mixtures of trioctylphosphate with either nonylphenol or isotridecanol. From the Table and the Figures, it can be seen that a 1:1 mixture of nonylphenol with trioctylphosphate on a molar basis at a total modifier to salicylaldoxime molar ratio of 0.426 gives equivalent performance to isotridecanol at a molar ratio of 0.426. With the mixture, however, the individual modifier components are present in a molar ratio of only 0.213. As can be seen from the data in the Table for the individual components, it is not an additive effect. Similar effects can be observed with isotridecanol and trioctylphosphate. In this case, however, one has to use a 2:1 ratio of isotridecanol to trioctylphosphate on a molar basis.

Another example of a mixture of modifier is the mixture of 0.01 molar tertiary amine, Alamine® 308/p-toluene sulfonic acid salt (ptsa) with various levels of isotridecanol (TDA). The results of the tests in which dodecylsalicylaldoxime was kept at 0.176 molar, can be seen in Tables 5 and 5B below, in which the first two runs Table 5A were made with 0.01 molar Alamine® 308/ptsa salt. In Table 5B, the runs were made without the Alamine 308-ptsa salt and with no modifier.

TABLE 5A

| TDA Molarity | Strip Point | Extraction Point | Net Transfer | Degree of Mod. |
|---|---|---|---|---|
| 0.0225 | 2.04 | 4.58 | 2.54 | 0.79 |
| 0.045 | 1.82 | 4.48 | 2.66 | 0.70 |

TABLE 5B

| Alamine ® 308 Molarity | Strip Point | Extraction Point | Net Transfer | Degree of Mod. |
|---|---|---|---|---|
| 0.0125 | 1.97 | 4.44 | 2.47 | 0.76 |
| 0.025 | 1.43 | 3.87 | 2.44 | 0.55 |
| TDA Molarity | | | | |
| 0.075 | 1.84 | 4.58 | 2.74 | 0.71 |
| No modifier | 2.59 | 4.97 | 2.38 | 1.00 |

What is claimed is:

1. A water insoluble reagent composition comprising an aldoxime extractant and an equilibrium modifier selected from the group consisting of aliphatic, aromatic and araliphatic compounds containing up to 36 carbon atoms in a molar ratio of aldoxime to modifier of 0.2 to about 1.5 so as to provide a net copper transfer greater than that achieved in the absence of modifier, and up to about 20% by weight of a kinetic additive, said modifier being selected from the group consisting of:

(i) a carboxylic acid ester selected from the group consisting of
    (a) a branched ester having a ratio of methyl groups to non-methyl groups less than 1:5;
    (b) an ester of a monocarboxylic acid selected from the group consiting of:
        methyl decanoate;
        2-pentyl octanoate;
        n-hexyl octanoate;
    (c) an ester of a diol having up to 6 carbon atoms and a monocarboxylic acid containing about 6–16 carbon atoms; and
    (d) an alkyl ester of a dicarboxylic acid wherein the alkyl group contains from 1 to about 6 carbon atoms and the dicarboxylic acid contains from about 4 to about 12 carbon atoms;
(ii) polyethers;
(iii) ethers other than nonyl anisole;
(iv) ester ethers;
(v) ketones;
(vi) nitriles;
(vii) carbonates;
(viii) an amide selected from the group consisting of:
    N,N'-di(2-ethylhexyl) urea;
    N,N-bis-2-ethylhexyl 2 ethyl hexanamide;
    N-hexyl 2-ethylhexanamide;
    N,N-dibutyl 2-ethyl hexanamide;
    N,N-dibutylbenzamide;
    N,N-dibutyl octanamide;
    N,N-dimethyl octanamide, and
    N,N-bis-2-ethylhexyl versatamide;
sulfoxides;
(x) carbamates; and
(xi) salts of amines and quaternary ammonium compounds.

2. A reagent composition as defined in claim 1, wherein said aldoxime is an hydroxy aryl aldoxime of the formula:

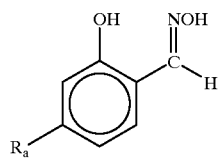

in which a has a value of 1, 2, 3 or 4, R is a saturated aliphatic group of about 1 to about 25 carbon atoms or an ethylenically unsaturated aliphatic group of 3 to about 25 carbon atoms, and the total number of carbon atoms in $R_a$ is from 3 to about 25.

3. An extraction reagent composition as defined in claim 1, wherein said aldoxime extractant is selected from the group consisting of 2-hydroxy-5-heptylbenzaldoxime, 2-hydroxy-5-octylbenzaldoxime, 2-hydroxy-5-nonylbenzaldoxime and 2-hydroxy-5-dodecyl benzaldoxime.

4. An extraction reagent composition as defined in claim 1 wherein said aldoxime extractant is 2-hydroxy-5-dodecylbenzaldoxime.

5. An extraction reagent composition as defined in claim 1 wherein the aldoxime extractant is 2-hydroxy-5-nonylbenzaldoxime.

6. An extraction reagent composition as defined in claim 1, wherein said ester (c) is 1,4-butane diol dihexanoate.

7. An extraction reagent composition as defined in claim 1 wherein in ester (d) said dicarboxylic acid is adipic acid and the alkyl group is selected from the group consisting of isobutyl and butyl.

8. An extraction reagent composition as defined in claim 2, wherein said modifier is an ester-ether.

9. An extraction reagent composition as defined in claim 8, wherein the ester-ether is selected from the group consisting of bis-2-ethoxyethyl adipate, dipropylene glycol dibenzoate, propylene glycol dibenzoate and polypropylene dibenzoate.

10. An extraction reagent composition as defined in claim 2, wherein said modifier is polyether.

11. An extraction reagent as defined in claim 10, wherein said ether is selected from the group consisting of benzyl 2-alkoxy alkyl ethers in which the alkoxy group contains from 2 to about 6 to about 6 carbon atoms and the alkyl group contains from 1 to about 6 carbon atoms.

12. An extraction reagent composition as defined in claim 11, wherein the benzyl ether is selected from the group consisting of benzyl 2-(2-butoxyethoxy) ethyl ether and benzyl 2-butoxy ethyl ether.

13. An extraction reagent as defined in claim 2, wherein said modifier is an alkyl carbonate in which the alkyl group contains from about 4 to about 16 carbon atoms.

14. An extraction reagent composition as defined in claim 13, wherein said carbonate is selected from the group consisting of isobutyl carbonate, isotridecyl carbonate and a mixed 8 and 10 carbon atom alkyl carbonate.

15. An extraction reagent composition as defined in claim 2, wherein said modifier is an alkyl ketone in which the alkyl group contains from about 1 to about 20 carbon atoms.

16. An extraction reagent composition as defined in claim 15, wherein the ketone is selected from the group consisting of isobutyl heptyl ketone, diundecyl ketone and 5,8-diethyldodecane-6,7-dione.

17. An extraction reagent composition as defined in claim 2, wherein said modifier is a nitrile having an aliphatic or araliphatic hydrocarbon group containing from about 10 to about 36 carbon atoms.

18. An extraction reagent composition as defined in claim 17, wherein said nitrile is selected from the group consisting of undecyl cyanide, the dinitrile of an oxo acid containing about 21 carbon atoms, oleonitrile and the dinitrile of a dimerized unsaturated 18 carbon atom fatty acid having about 36 carbon atoms.

19. An extraction reagent composition as defined in claim 2, wherein said carbamate is selected from the group consisting of N-octyl isotridecylcarbamate and isotridecyl N-tolylcarbamate.

20. An extraction reagent composition as defined in claim 2, wherein said modifier is a sulfoxide.

21. An extraction reagent composition as defined in claim 20, wherein said sulfoxide is di-2-ethylhexyl sulfoxide.

22. An extraction reagent composition as defined in claim 2, wherein said modifier is a salt of an amine compound selected from the group consisting of tertiary amines and quaternary ammonium compounds containing alkyl groups having from about 8 to about 18 carbon atoms.

23. An extraction reagent composition as defined in claim 22, in which said salt is a sulfonic acid salt.

24. An extraction reagent composition as defined in claim 23, wherein the salt is selected from the group consisting of the dinonylnaphthalene sulfonic acid and toluene sulfonic acid salts.

25. A water insoluble, water-immiscible hydrocarbon solvent solution of the extraction reagent composition defined in claim 2.

26. A solvent solution as defined in claim 25, wherein the hydrocarbon solvent is kerosene.

27. A process for recovery of copper from an aqueous solution containing copper values comprising (1) contacting the aqueous solution with an organic phase comprising a water insoluble and water immiscible solvent solution of the extraction reagent composition defined in claim 2, to extract at least a portion of the copper values into the organic phase;

(2) separating the resultant copper pregnant organic phase from the resultant copper barren aqueous phase; and (3) recovering the copper values from the copper pregnant organic phase.

28. A process as defined in claim 27, wherein the water immiscible solvent is kerosene.

29. A process as defined in claim 27, wherein the recovering of the copper values from the copper pregnant organic phase of step (3) comprises stripping the copper values from the copper pregnant organic phase by contacting the copper pregnant organic phase with an aqueous acid solution.

30. A metal aldoxime extractant modifier compound selected from the group consisting of:

(i) tridecyl-N-tolyl carbamate, (ii) N-octyl isotridecylcarbamate, (iii) N,N'-bis 2-ethylhexyl 2-ethylhexanamide, and (iv) N-hexyl 2-ethylhexanamide.

* * * * *